United States Patent [19]
Walcott et al.

[11] Patent Number: 5,697,928
[45] Date of Patent: Dec. 16, 1997

[54] CARDIC ELECTRODE CATHETER

[75] Inventors: Gregory P. Walcott, Wilsonville;
Raymond E. Ideker, Birmingham, both of Ala.; Jay Alan Warren, North Oaks, Minn.

[73] Assignee: UAB Research Foundation, Birmingham, Ala.

[21] Appl. No.: 717,371

[22] Filed: Sep. 23, 1996

[51] Int. Cl.⁶ ................................................ A61B 17/39
[52] U.S. Cl. .......................... 606/41; 607/116; 607/119; 607/122; 607/123
[58] Field of Search .................... 606/41; 607/4, 607/5, 119, 122, 15, 99, 128, 148

[56] References Cited

U.S. PATENT DOCUMENTS

| | | | |
|---|---|---|---|
| 4,860,769 | 8/1989 | Fogarty et al. | 128/786 |
| 5,016,808 | 5/1991 | Heil, Jr. et al. | 228/176 |
| 5,133,365 | 7/1992 | Heil, Jr. et al. | 128/786 |
| 5,239,999 | 8/1993 | Imran | 128/642 |
| 5,374,287 | 12/1994 | Rubin | 607/131 |
| 5,383,917 | 1/1995 | Desai et al. | 607/702 |
| 5,397,342 | 3/1995 | Heil, Jr. et al. | 607/129 |
| 5,423,865 | 6/1995 | Bowald et al. | 607/5 |
| 5,431,683 | 7/1995 | Bowald et al. | 607/5 |
| 5,462,545 | 10/1995 | Wang et al. | 606/41 |
| 5,487,385 | 1/1996 | Avitall | 607/99 |
| 5,545,193 | 8/1996 | Fleischman et al. | 607/119 |
| 5,549,661 | 8/1996 | Kordis et al. | 607/99 |
| 5,551,427 | 9/1996 | Atlmann | 607/128 |
| 5,575,766 | 11/1996 | Swartz et al. | 607/15 |
| 5,575,810 | 11/1996 | Swanson et al. | 607/148 |

*Primary Examiner*—Jennifer Bahr
*Assistant Examiner*—David M. Ruddy
*Attorney, Agent, or Firm*—Gifford, Krass, Groh, Sprinkle, Patmore, Anderson & Citkowski, P.C.

[57] ABSTRACT

An electrode catheter is disclosed for creating a linear lesion in heart tissue of a heart chamber in order to correct cardiac arrhythmia. The catheter is elongated in dimension such that, upon insertion of the catheter in the patient, the catheter substantially continuously contacts either the endocardial or epicardial heart tissue. The catheter includes a plurality of electrodes and the electrodes are positioned at spaced intervals along the catheter. The electrodes are then sequentially energized with a radio frequency in conjunction with a back plate attached to the patient such that the electrodes form a continuous lesion conforming in shape to the shape of the catheter on the heart tissue. This lesion, furthermore, is of sufficient depth such that the lesion interrupts electrical nodal conduction across the lesion.

17 Claims, 1 Drawing Sheet

CARDIC ELECTRODE CATHETER

BACKGROUND OF THE INVENTION

I. Field of the Invention

The present invention relates generally to catheters and, more particularly, to a cardiac electrode catheter.

II. Description of the Prior Art

In order to prevent, or at least reduce the possibility of, arrhythmia, such as atrial fibrillation, the prior surgical treatment has consisted primarily of the maze procedure. In the maze procedure, the left and right atria are divided into small areas so that there will be an insufficient region of atrial tissue to support fibrillation and yet still provide a pathway from the S-A node to the A-V node to allow for normal initiation of the heartbeat.

A disadvantage of the maze procedure, however, is that it is open heart surgery entailing relatively high risk for the patient.

More recently, a closed chest procedure has been developed to ablate atrial fibrillation by making a series of linear radio frequency burns in the left and right atrium. These burns are made by slowly dragging the tip of an ablation catheter across the endocardial surface. This catheter creates a lesion on the interior of the surface which, if performed correctly, prevents conductance between two regions of cardiac tissue across the lesion. In essence, this more recently developed procedure reproduces, or at least simulates, the previously known maze procedure.

The use of an ablation catheter to create a drag lesion suffers from several disadvantages. In particular, the failure of the operator to maintain constant contact between the catheter and the heart tissue along the entire length of the lesion would not only be ineffective for preventing the arrhythmia, but may also increase the likelihood of the arrhythmia.

BRIEF DESCRIPTION OF THE PRESENT INVENTION

The present invention provides a device for creating a linear lesion in endocardial heart tissue which overcomes all of the above-mentioned disadvantages of the previously known devices and procedures.

In brief, the present invention comprises an elongated catheter which is insertable either into or along the outer surface of the heart chamber. The catheter is dimensioned such that, upon insertion into or on the heart chamber, the catheter substantially continuously contacts the endocardial or epicardial heart tissue of the chamber, respectively.

The catheter includes a plurality of spaced electrodes along its length. Additionally, an electrically conductive plate is preferably, but optionally, placed in abutment with an external surface of the patient's body.

In order to create the lesion, a radio frequency generator selectively and sequentially energizes adjacent electrodes and the external plate, which is preferably maintained at ground if present, with a radio frequency energy sufficient to ablate the endocardial or epicardial heart tissue and create a lesion. The conduction between adjacent energized electrodes ensures that the lesion is continuous between the electrodes while electrical conduction between the electrodes and the external plate, if present, ensures that the lesion is of sufficient depth to prevent conduction between two regions of cardiac tissue.

Although in the preferred embodiment, the electrode catheter is utilized to create an elongated lesion in or on the atria to prevent atrial fibrillation, it may alternatively be used to create a lesion to prevent ventricular tachycardia or other types of arrhythmia.

BRIEF DESCRIPTION OF THE DRAWING

A better understanding of the present invention will be had upon reference to the following detailed description when read in conjunction with the accompanying drawing, wherein like reference characters refer to like parts throughout the several views, and in which.

Detailed Description of a Preferred Embodiment of the Present Invention

Figure 1:
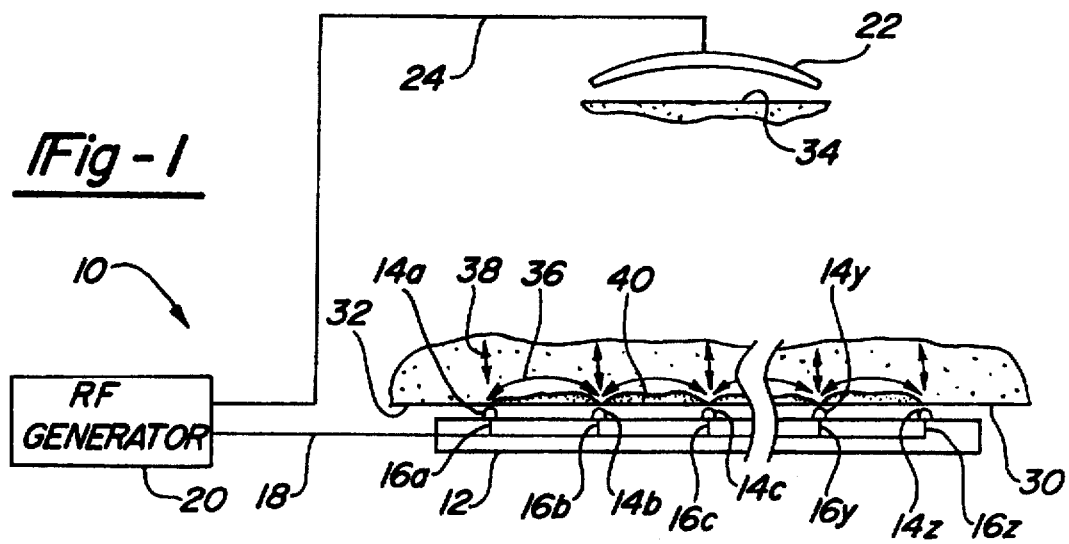
FIG. 1 is a diagrammatic view illustrating a preferred embodiment of the present invention.

With reference first to FIG. 1, a diagrammatic view illustrating a preferred embodiment of the device 10 of the present invention is there shown and comprises an elongated catheter 12 having a plurality of electrodes $14a, 14b, 14c, \ldots 14y$ and $14z$ provided at spaced intervals along its length. Preferably, each electrode $14a-14z$ is spaced between 2–3 mm from its adjacent electrodes along the catheter 12. Typically, 25–30 electrodes $14a-14z$ are provided along the length of the catheter 12 although other numbers of electrodes may be used without deviation from the spirit or scope of this invention.

An electrical wire $16a, 16b \ldots 16z$ is electrically connected to each respective electrode $14a-14z$. These electrical wires $16a-16z$ are then electrically connected through a wire bundle 18 to a radio frequency generator 20. Additionally, an electrically conductive external plate 22 is also preferably, but optionally, electrically connected by a wire 24 to the radio frequency generator 20, preferably as the ground input.

The radio frequency generator 20 preferably generates a radio frequency in the range of 350 kilohertz–500 kilohertz. Furthermore, the radio frequency generator 20 is preferably a multi-channel polyphase radio frequency generator and, as such, generates a radio frequency signal to at least two adjacent electrodes $14a-14z$ via their respective electrical wires $16a-16z$. Preferably, the radio frequency radio generator 20 has a power output of about 10 watts per channel, i.e. 10 watts per each electrode $14a-14z$ which is energized by the generator 20.

Figure 2:
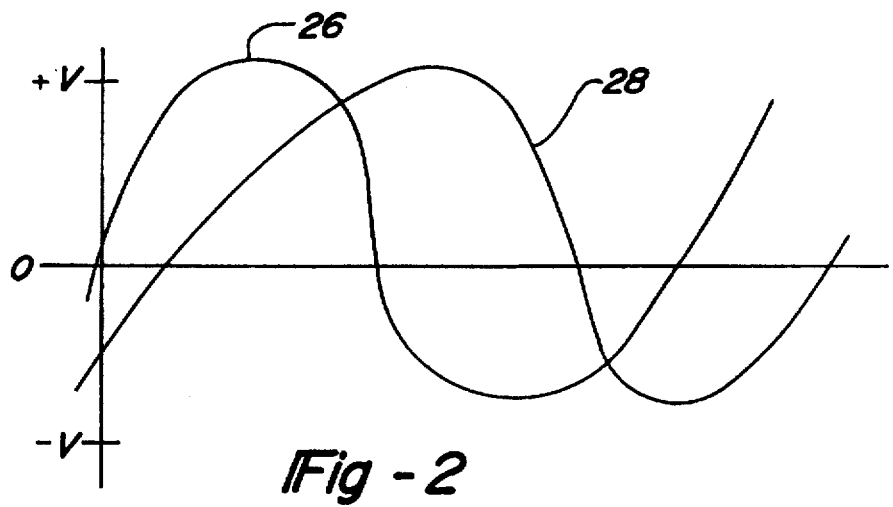
FIG. 2 is a graph illustrating the energization of the preferred embodiment of the present invention.

With reference now to FIG. 2, two voltage wave forms 26 and 28 are there shown which represent the output signal from the radio frequency generator 20 to two adjacent electrodes 14. The wave forms 26 and 28 are offset in phase from each other in a range between 0–180 degrees, and preferably of 45–180 degrees and, more preferably, of about 130 degrees. Furthermore, although only two wave forms are illustrated in FIG. 2 as output signals from the radio frequency generator 20, it will be understood that more than two adjacent electrodes $14a-14z$ may be simultaneously energized by the generator 20. Alternatively, the ground plate and the two electrodes could each be driven with a voltage out of phase from the other two. This would result in a three-phase system. Electrodes could be added to this system, each out of phase with each other and the ground plate to create a multiphase system.

The radio frequency generator 20 also preferably includes means for continuously varying the phase offset between the radio frequency signals to adjacent electrodes between a preselected lower limit, e.g. 0 degrees, and a preselected upper limit, e.g. 180 degrees. By varying the phase offset, and thus the frequency, of the signals, the depth and width of the lesion can be carefully controlled.

Referring again to FIG. 1, in practice, the catheter 12 is introduced into a heart chamber 30 such that the catheter 12, and thus the electrodes 14a–14z, continuously contact the endocardial heart tissue 32 forming the heart chamber. Any conventional procedure, such as aortal or venal insertion, may be utilized to introduce the catheter 12 into the heart chamber 30. Furthermore, the heart chamber 30 may be an atrium if correction of atrial fibrillation is desired or, alternatively, a ventricle for the correction of ventricular tachycardia or other arrhythmia.

Alternatively, the catheter 12 is introduced into the pericardial space such that the electrodes 14a–14z continuously contact the epicardial heart tissue forming the heart tissue to be treated.

Additionally, the external plate 22 is preferably applied to an external surface 34 of the patient such as the patient's back. In the well known fashion, the plate 22 provides the ground plate return to the generator 20.

Following insertion of the catheter 12 into the heart chamber 30 or onto the epicardial surface of the heart and the positioning of the external plate 22 on the external surface 34 of the patient, the radio frequency generator 20 is activated so that at least two adjacent electrodes 14 are energized with the wave forms illustrated in FIG. 2. Assuming that the two adjacent electrodes are 14a and 14b, the energization of the electrode 14a and 14b creates a radio frequency current between the electrodes 14a and 14b as illustrated diagrammatically by arrow 36. Activation of the electrodes 14a and 14b also causes electrical conduction between the electrodes 14a and 14b and the external plate 22 as depicted by arrows 38. The power output from the generator 20, as well as the duration of the energization of the adjacent electrodes 14a and 14b, is sufficient to create a continuous lesion 40 between the electrodes 14a and 14b of a depth and width sufficient to prevent cardiac tissue conduction across the lesion 40. In practice, a power output of approximately 10 watts per channel at the selected frequency of 350 kilohertz–500 kilohertz for approximately one to two minutes is sufficient to create a lesion of approximately 4 mm in depth and width which is sufficient to prevent such cardiac nodal conduction.

If the external plate 22 is omitted, the lesion is created by conduction between the adjacent electrodes 14a14 z.

Following creation of the lesion in the above-described fashion between the electrodes 14a and 14b, the radio frequency generator 20 is then electrically connected to the next adjacent electrodes, i.e. 14b and 14c, wherein the above process is repeated and so on throughout each of the electrodes 14 on the catheter 12. In doing so, a continuous lesion is provided from the first to the last electrode or at least between the first and last selected electrode 14 necessary to form the desired length of the lesion.

Following the creation of the lesion, the catheter is removed in the conventional fashion.

It will be understood, of course, that it is only necessary to energize adjacent electrodes 14 on the catheter 12 sufficient to obtain the desired length of the lesion. For example, if a shorter lesion is desired, only the middle electrodes, e.g. 14c–14y, would be activated.

Similarly, although the present invention has been described as only sequentially energizing two adjacent electrodes, it will be understood, of course, that multiple adjacent electrodes, such as three or even more, up to the total number of electrodes on the catheter, may be simultaneously energized by the radio frequency generator 20.

Figure 3:
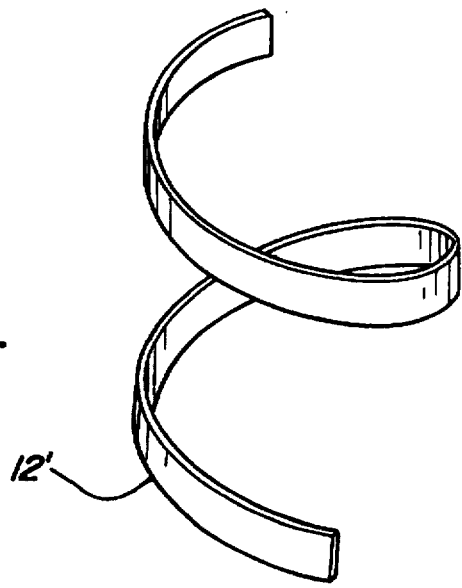
FIG.3 is an elevational view illustrating a further preferred embodiment of the invention.

It will be further understood that the catheter 12 may assume any arbitrary shape necessary to obtain the desired lesion shape. For example, the catheter 12 may be linear as shown in FIG. 1. Alternatively, however, the catheter 12' may be helical in shape in order to form a helical shaped lesion as shown in FIG. 3. Any other shape is also obtainable.

From the foregoing, it can be seen that the present invention provides a novel means for creating an elongated lesion in the endocardial tissue of a heart chamber. Unlike the previously known maze procedure, the present invention assures that the lesion is formed continuously between the desired ends of the lesion thus avoiding gaps in the lesion or incision that might otherwise occur with the previously known maze procedure through surgeon error.

Having described our invention, however, many modifications thereto will become apparent to those skilled in the art to which it pertains without deviation from the spirit of the invention as defined by the scope of the appended claims.

We claim:

1. A device for creating a linear lesion in heart tissue forming a heart chamber of a patient comprising:

an elongated catheter, said catheter having a plurality of electrodes, said electrodes being positioned at spaced intervals along the catheter, said catheter being dimensioned such that, upon insertion of said catheter into the patient, said electrodes contact the heart tissue, means for electrically energizing said electrodes so that the energization of said electrodes forms a substantially continuous lesion conforming in shape to the shape of the catheter on the heart tissue without physical movement of said catheter, said lesion being of sufficient depth such that the lesion interrupts electrical conduction between two regions of cardiac tissue across the lesion an electrical conduction plate in contact with an external portion of the patient and wherein said energization means comprises means for electrically energizing adjacent electrodes on said catheter to produce current flow between said adjacent electrodes and between each electrode and said electrical conduction plate wherein said energizing means comprises means for sequentially electrically energizing adjacent electrodes on said catheter from a position adjacent one end of said catheter to a position spaced from said one end of said catheter to produce current flow between said adjacent electrodes and between each electrode and said electrical conduction plate and wherein said radio frequency generator comprises a polyphase radio frequency generator.

2. The invention as defined in claim 1 wherein said catheter extends between two cardiac nodes.

3. The invention as defined in claim 1 wherein said radio frequency generates a frequency in the range of 350 kilohertz to 500 kilohertz.

4. The invention as defined in claim 1 wherein the heart chamber is an atrium and wherein said catheter divides the atria into cardiac regions while maintaining conduction between the S-A node and the A-V node.

5. The invention as defined in claim 1 wherein said radio frequency signal to said adjacent electrodes are offset in phase from each other by 45–180 degrees.

6. The invention as defined in claim 5 wherein said radio frequency signal to said adjacent electrodes are offset in phase from each other by substantially 180 degrees.

7. The invention as defined in claim 1 wherein said radio frequency generator generates substantially 10 watts of power to each electrode.

8. The invention as defined in claim 1 wherein said catheter is helical in shape.

9. The invention as defined in claim 1 wherein said energizing means comprises means for simultaneously energizing a plurality of adjacent electrodes.

10. The invention as defined in claim 9 wherein said plurality of electrodes comprises at least three electrodes.

11. The invention as defined in claim 9 wherein said plurality of electrodes comprises at least four electrodes.

12. The invention as defined in claim 9 wherein said plurality of electrodes comprises all of said electrodes.

13. A method for modifying conduction between two regions of heart tissue of a heart chamber between two cardiac nodes of a patient comprising the steps of:

placing an elongated catheter on the heart tissue so that the catheter contacts and divides the heart tissue between the cardiac nodes into at least two cardiac regions, said catheter having a plurality of electrodes at spaced positions therealong, placing an electrical conduction plate on the patient, electrically energizing said electrodes to create a substantially continuous lesion along the length of the catheter of sufficient depth to prevent conduction between two regions of cardiac tissue across the lesion wherein said energizing step comprises the step of sequentially energizing said adjacent electrodes from a position adjacent one end of the catheter to a position spaced from said one end of said catheter with a polyphase radio frequency signal to produce current flow between said adjacent electrodes and between each electrode and said electrical conduction plate.

14. The invention as defined in claim 13 wherein said energizing step further comprises the step of energizing at least three adjacent electrodes simultaneously.

15. The invention as defined in claim 13 wherein said energizing means comprises a radio frequency generator having at least two signal outputs electrically connected to adjacent electrodes.

16. The invention as defined in claim 15 wherein said at least two signal outputs are offset in phase with respect to each other between 0 and 180 degrees.

17. The invention as defined in claim 15 and comprising means for continuously varying a phase offset between said signal outputs between a preselected lower limit and a preselected upper limit.

* * * * *